United States Patent
Sato et al.

(10) Patent No.: US 11,178,340 B2
(45) Date of Patent: Nov. 16, 2021

(54) CONTROL DEVICE, MEDICAL OBSERVATION SYSTEM, CONTROL METHOD, AND COMPUTER READABLE RECORDING MEDIUM

(71) Applicant: Sony Olympus Medical Solutions Inc., Tokyo (JP)

(72) Inventors: Narumi Sato, Tokyo (JP); Ryohei Kagawa, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/904,586

(22) Filed: Jun. 18, 2020

(65) Prior Publication Data
US 2021/0037176 A1 Feb. 4, 2021

(30) Foreign Application Priority Data

Jun. 28, 2019 (JP) .............................. JP2019-122380

(51) Int. Cl.
| | | |
|---|---|---|
| H04N 5/235 | (2006.01) |
| H04N 5/225 | (2006.01) |
| H04N 7/18 | (2006.01) |
| G10L 25/03 | (2013.01) |
| A61B 1/045 | (2006.01) |
| A61B 1/06 | (2006.01) |
| A61B 1/267 | (2006.01) |
| G10L 25/48 | (2013.01) |

(52) U.S. Cl.
CPC ............ *H04N 5/2354* (2013.01); *A61B 1/045* (2013.01); *A61B 1/0684* (2013.01); *A61B 1/2673* (2013.01); *G10L 25/03* (2013.01); *G10L 25/48* (2013.01); *H04N 5/2253* (2013.01); *H04N 5/2256* (2013.01); *H04N 7/18* (2013.01); *H04N 2005/2255* (2013.01)

(58) Field of Classification Search
CPC .. H04N 5/2354; H04N 5/2253; H04N 5/2256; H04N 7/18; H04N 2005/2255; G10L 25/03; G10L 25/48; A61B 1/045; A61B 1/0684; A61B 1/2673
See application file for complete search history.

(56) References Cited

U.S. PATENT DOCUMENTS

| | | | | |
|---|---|---|---|---|
| 2015/0124124 A1* | 5/2015 | Maeyama | ............ | H04N 5/2356 348/235 |
| 2015/0272429 A1* | 10/2015 | Shigeta | ............... | A61B 1/0002 348/65 |
| 2019/0142265 A1* | 5/2019 | Bos | ...................... | A61B 1/2673 600/188 |

FOREIGN PATENT DOCUMENTS

JP 5948512 B2 7/2016

\* cited by examiner

*Primary Examiner* — Nasim N Nirjhar
(74) *Attorney, Agent, or Firm* — Xsensus, LLP (57) ABSTRACT

A control device includes: a hardware processor; and a memory, wherein the hardware processor is configured to: control an image sensor configured to generate an image signal by performing imaging sequentially according to predetermined frames; detect a frequency of vocal cord vibration of a subject based on a voice signal; set a pulse width and a light emission cycle for when a light source emits light, based on the frequency and a preset duty cycle; control the light source to emit the pulse light using the pulse width and the light emission cycle in one field period or one frame period of the image sensor in synchronization with the frequency; calculate, based on the light emission cycle or the frequency, a gain amount by which the image signal is to be multiplied; and multiply the image signal by the gain amount.

9 Claims, 6 Drawing Sheets

CONTROL DEVICE, MEDICAL OBSERVATION SYSTEM, CONTROL METHOD, AND COMPUTER READABLE RECORDING MEDIUM

This application claims priority from Japanese Application No. 2019-122380, filed on Jun. 28, 2019, the contents of which are incorporated by reference herein in its entirety.

BACKGROUND

The present disclosure relates to a control device that performs image processing of images, a medical observation system, a control method, and a computer readable recording medium.

In an endoscope system, observation of the vocal cords of a subject such as a person or an animal is sometimes performed by causing white light to be emitted intermittently. As such an endoscope system that performs observation of the vocal cords of a subject, a technology is known that performs strobe observation, in a stop state or a slow-motion state, of vocal cords that are vibrating at high speed by emitting pulse-like illumination light in synchronization with the vibrational frequency of the vocal cords. In strobe observation, the reading timing of the image sensor and the illumination timing are asynchronous, and therefore, even in cases where a period in which all the pixels may be commonly exposed is adequately secured, the illumination timing sometimes overlaps with the reading timing, the exposure amount differs between images, variations in brightness between images may not be eliminated, and maintaining image quality has not been possible.

Therefore, in Japanese Patent Publication No. 5948512, image quality may be maintained, even in cases where pulse light is emitted with any timing relative to the reading timing of an image sensor, by generating an image based on a one-frame image signal (a pseudo image signal) obtained through exposure equivalent to one pulse of the pulse light, based on first pixel signals, which are one frame's worth of an image signal and read out with reading timing that includes a pulse-light illumination period, and one frame's worth of second pixel signals, which are read out with reading timing after one frame of the first pixel signals, the image being generated by synthesizing pixel signals which correspond to an overlap line among the first pixel signals and pixel signals which correspond to an overlap line among the second pixel signals, wherein an overlap line is configured by an overlap between a pulse-light illumination period and reading timing among a plurality of pixels in an image sensor.

SUMMARY

However, in Japanese Patent Publication No. 5948512, there is a problem in that, when the duty cycle indicating the ratio between one frame period and the total emission period in the one frame period is fixed, the pulse-light emission time is inversely proportional to the vocal cord frequency, and hence the higher the vocal cord frequency, the shorter the pulse-light emission time is, whereby the exposure amount is then small and the image grows dark.

There is a need for a control device that performs image processing of images, a medical observation system, a control method, and a computer readable recording medium that enable image brightness to be maintained constant regardless of a vocal cord frequency.

According to one aspect of the present disclosure, there is provided a control device including: a hardware processor; and a memory, wherein the hardware processor is configured to: control an image sensor including a plurality of pixels arranged in a two-dimensional matrix to generate an image signal by performing imaging sequentially according to predetermined frames; detect a frequency of vocal cord vibration of a subject based on a voice signal input from an external device; set, for a light source configured to intermittently emit pulse light according to a pulse current, a pulse width and a light emission cycle for when the light source emits light, based on the frequency and a preset duty cycle; control the light source to emit the pulse light using the pulse width and the light emission cycle in one field period or one frame period of the image sensor in synchronization with the frequency; calculate, based on the light emission cycle or the frequency, a gain amount by which the image signal is to be multiplied; and multiply the image signal by the gain amount.

DETAILED DESCRIPTION

Embodiments of the present disclosure will be described in detail hereinbelow in conjunction with the drawings. Note that the present disclosure is not limited to or by the following embodiments. Furthermore, the respective drawings referenced in the following description merely provide an approximate illustration of shapes, sizes, and positional relationships to an extent enabling an understanding of the content of the present disclosure. That is, the present disclosure is not limited to or by the shapes, sizes, and positional relationships illustrated in the respective drawings. Furthermore, the disclosures of the drawings are described by assigning the same reference signs to the same parts. In addition, as an example of a medical observation system according to the present disclosure, an endoscope system capable of observing vocal cords will be described.

First Embodiment

Overall Configuration of Endoscope System

Figure 1:
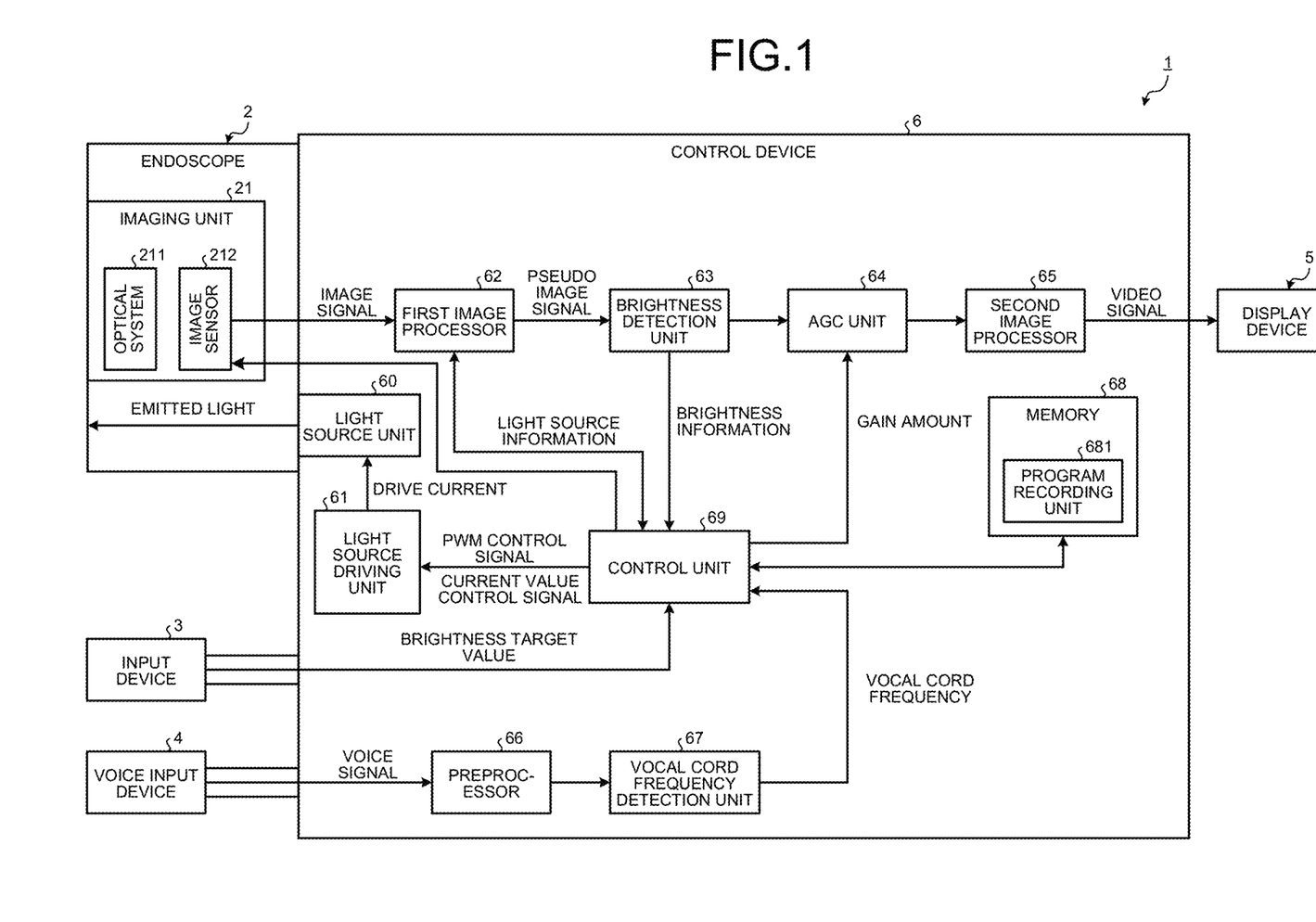
FIG. 1 is a block diagram illustrating a function configuration of an endoscope system according to a first embodiment.

FIG. 1 is a block diagram illustrating a function configuration of an endoscope system according to a first embodiment. The endoscope system 1 illustrated in FIG. 1 is used in the medical field and enables strobe observation of vocal cords serving as an object. The endoscope system 1 includes an endoscope 2, an input device 3, a voice input device 4, a display device 5, and a control device 6.

The endoscope 2 is inserted into a subject such as a living body. The endoscope 2 projects emitted light (pulse light) supplied from the control device 6, described subsequently, toward the object from the end portion of an insertable section 20, and generates an image signal for an object image by receiving light that is reflected from the object. The endoscope 2 includes an imaging unit 21 at least at the end portion of the insertable section 20.

The imaging unit 21 includes an optical system 211 and an image sensor 212. The optical system 211 includes one or a plurality of lenses and forms an object image from the object on a light-receiving surface of the image sensor 212. Based on control by the control device 6, the image sensor 212 receives the object image formed by the optical system 211 according to a predetermined frame rate and generates an image signal by photoelectrically converting the received object image. The image sensor 212 outputs the image signal to the control device 6. The image sensor 212 includes a charge coupled device (CCD) sensor of an interlace scan system. Furthermore, the image sensor 212 includes a plurality of pixels arranged in a two-dimensional matrix.

The input device 3 receives user operations by a user such as a doctor and outputs operation signals that correspond to the received user operations to the control device 6. The input device 3 includes a keyboard, a mouse, switches, buttons, a foot switch and a touch panel, or the like.

Based on control by the control device 6, the voice input device 4 receives inputs of voice emitted from the vocal cords and makes outputs to the control device 6 by converting this voice to a voice signal. The voice input device 4 includes a microphone or the like.

Based on control by the control device 6, the display device 5 displays a display image based on a video signal which is input from the control device 6. The display device 5 includes a display that employs liquid crystals or organic electroluminescence (EL), or the like.

The control device 6 includes at least one or more processors that include a memory and hardware such as a central processing unit (CPU), an field-programmable gate array (FPGA), and a graphics processing unit (GPU). The control device 6 integrally controls the operations of each of the parts included in the endoscope system 1. The control device 6 includes a light source unit 60, a light source driving unit 61, a first image processor 62, a brightness detection unit 63, an autogain controller unit 64 (called "AGC unit 64" hereinbelow), a second image processor 65, a preprocessor 66, a vocal cord frequency detection unit 67, a memory 68, and a control unit 69.

The light source unit 60 emits pulse light intermittently using a predetermined intensity and light emission cycle based on a drive current which is input from the light source driving unit 61. The light source unit 60 includes a white LED (light emitting diode) and a condenser lens, or the like. The pulse light emitted by the light source unit 60 is emitted toward an object from the end of the endoscope 2. Note that the light source unit 60 is not limited to a white LED and may be configured capable of emitting white light by combining light which is emitted by a red LED, a blue LED, and a green LED, respectively.

Based on control by the control unit 69, the light source driving unit 61 causes the light source unit 60 to emit pulse light in a predetermined light emission cycle and to emit the pulse light at a predetermined intensity. Specifically, the light source driving unit 61 causes the light source unit 60 to emit light in a light amount corresponding to a predetermined pulse current value based on a PWM control signal and a current value control signal which are input from the control unit 69.

Based on the control unit 69, the first image processor 62 performs various image processing on the image signal which is input from the image sensor 212 of the endoscope 2 and makes outputs to the brightness detection unit 63. Here, the various image processing by the first image processor 62 is, with respect to a pixel signal, A/D conversion processing, optical black subtraction processing, white balance (WB) adjustment processing, demosaic processing (in the case of a configuration in which the image sensor 212 includes a Bayer array color filter (not illustrated)), color matrix arithmetic processing, gamma correction processing, color reproduction processing, and edge enhancement processing, and the like. In addition, the first image processor 62 generates a pseudo image signal based on light source information that is input from the control unit 69 and that relates to the light emission cycle of the light source unit 60, the current value supplied to the light source unit 60, and the pulse width of the pulse light. Specifically, the first image processor 62 generates, from an image signal of a plurality of continuous frames, a pseudo pixel signal that corresponds to a pixel signal in a case where all the pixels of the image sensor 212 are exposed in a pulse-light light emission period (light emission time) by the light source unit 60. More specifically, when generating the pseudo pixel signal, the first image processor 62 generates the pseudo pixel signal by using, for a specified horizontal line among horizontal lines of a plurality of pixels in the image sensor 212, an image signal which is obtained by multiplying a specified one frame's worth of an image signal from the respective pixels of the specified horizontal line by the ratio, of a specified pulse-light exposure amount resulting from exposure in a specified one frame, to the total exposure amount obtained by adding up all of the respective pulse-light exposure amounts resulting from exposure of the specified horizontal line in one specified frame that contains a specified pulse-light illumination period.

The brightness detection unit 63 detects the brightness of an image based on an image signal or a pseudo image signal (an image signal) which is input from the first image processor 62 and outputs brightness information relating to this brightness to the control unit 69. Here, brightness information is an average value for the luminance of each pixel in the image based on the pseudo image signal or image signal. Furthermore, the brightness detection unit 63 outputs the pseudo image signal, which has been input from the first image processor 62, to the AGC unit 64.

Based on the control unit 69, the AGC unit 64 adjusts the gain of the pseudo image signal, which has been input from the brightness detection unit 63, and the gain of a pseudo image signal to be output to the second image processor 65, to predetermined values and outputs the pseudo image signal to the second image processor 65. Specifically, the AGC unit 64 multiplies the image signal or the pseudo image signal by the gain amounts set by the control unit 69 and outputs the image signal or the pseudo image signal to the second image processor 65.

Based on the control unit 69, the second image processor 65 generates a video signal by performing various image processing on the pseudo image signal that has been input from the AGC unit 64 and outputs the video signal to the display device 5. For example, when the pseudo image signal is RGB data, the second image processor 65 performs image processing to convert RGB data to YCU data.

The preprocessor 66 amplifies a voice signal that has been input from the voice input device 4, performs A/D conversion processing on the amplified voice signal, and outputs the A/D converted signal to the vocal cord frequency detection unit 67. Note that the functions of the preprocessor 66 may also be provided in the voice input device 4.

Based on the voice signal that has been input from the preprocessor 66, the vocal cord frequency detection unit 67 detects the frequency of vibration of voice which is input to the voice input device 4. Specifically, the vocal cord frequency detection unit 67 detects a vocal cord vibrational frequency based on the voice signal that has been input from the preprocessor 66 and outputs the detected vocal cord vibrational frequency to the control unit 69.

The memory 68 records various information and the like which is executed by the endoscope system 1. The memory 68 includes a volatile memory, a nonvolatile memory, and a removable memory card, or the like. Furthermore, the memory 68 includes a program recording unit 681 that records various programs executed by the endoscope system 1.

The control unit 69 includes at least one or more processors that include a memory and hardware such as a CPU. The control unit 69 causes the image sensor 212 to generate an image signal through sequential imaging according to a predetermined frame rate of, for example, 60 fps or 50 fps and to output the image signal to the first image processor 62. Furthermore, the control unit 69 sets, for the light source unit 60, the pulse width (light emission time) and the light emission cycle (light emission frequency) for when the light source unit 60 emits light, based on the vocal cord vibrational frequency that has been input from the vocal cord frequency detection unit 67, and a preset duty cycle. In addition, the control unit 69 causes the light source unit 60 to emit pulse light toward the vocal cords using the pulse width and the light emission cycle which have been set and within one field period or one frame period of the image sensor 212 in synchronization with the vocal cord vibrational frequency which has been input from the vocal cord frequency detection unit 67. Furthermore, the control unit 69 sets, based on the light emission cycle of the light source unit 60, the gain amount by which the pseudo image signal is to be multiplied by the AGC unit 64.

Overview of Brightness Correction

Figure 2:
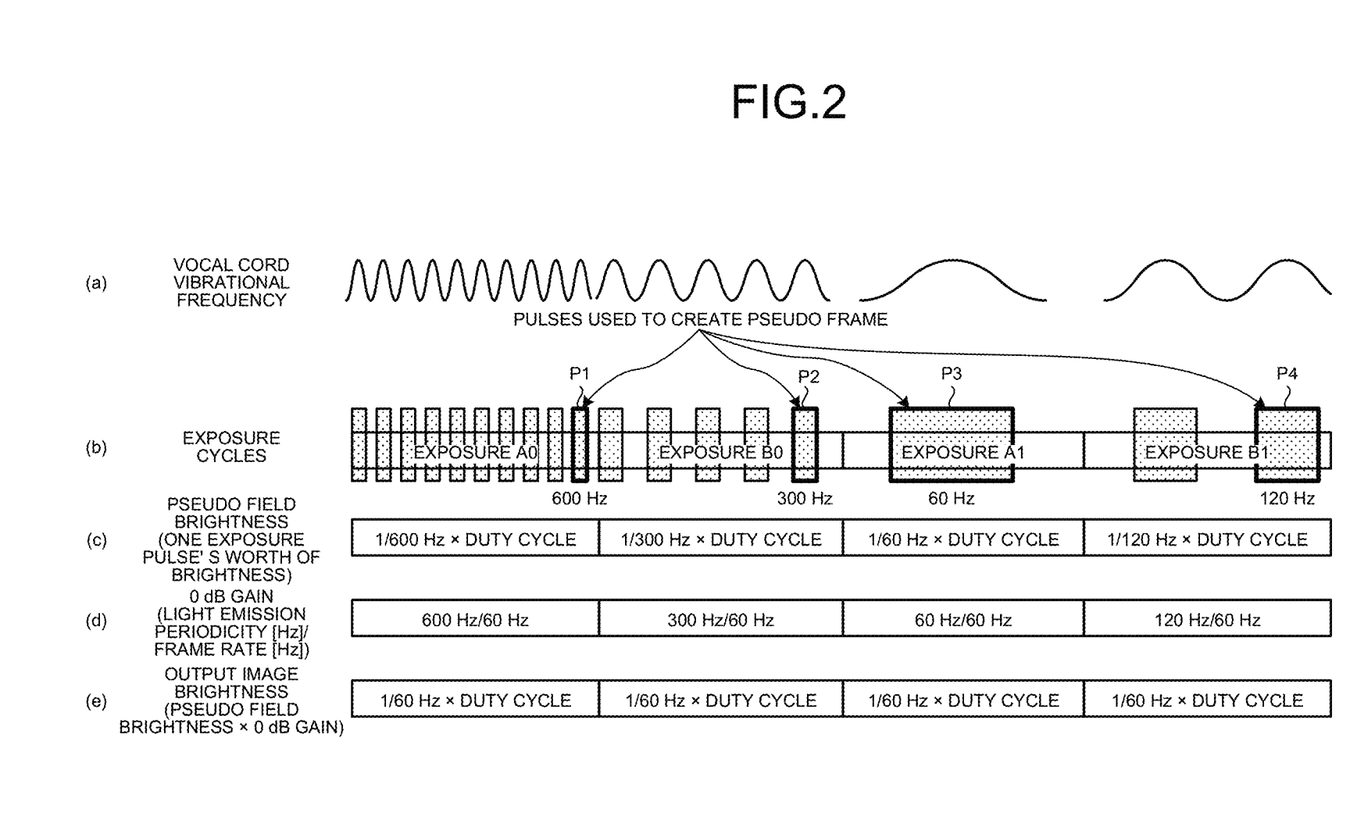
FIG. 2 is a diagram illustrating an overview of a correction method of correcting the brightness of a pseudo frame based on a pseudo image signal as performed by a control unit according to the first embodiment.

A method of correcting the brightness of a pseudo field based on a pseudo image signal as performed by the control unit 69 will be described next. FIG. 2 is a diagram illustrating an overview of a correction method of correcting the brightness of a pseudo field based on a pseudo image signal as performed by the control unit 69. In FIG. 2, starting at the top, (a) illustrates the vocal cord vibrational frequency, (b) illustrates the exposure period (light emission cycle (light emission frequency) and pulse width (light emission time)) in one field of the image sensor 212, (c) illustrates the brightness of one field based on a pseudo image signal, (d) illustrates 0 dB (gain amount) (light emission periodicity [Hz]/frame rate [Hz]) of the AGC unit 64, and (e) illustrates the brightness of an output image (the pseudo field brightness×0 dB gain).

As illustrated in FIG. 2, the control unit 69 sets a pulse width and a light emission cycle for when the light source unit 60 emits pulse light in one field period of the image sensor 212, based on the vocal cord vibrational frequency detected by the vocal cord frequency detection unit 67 and the duty cycle, and causes the light source unit 60 to emit light using the set pulse width and light emission cycle. Specifically, as illustrated in FIG. 2, when the vocal cord vibrational frequency detected by the vocal cord frequency detection unit 67 is 600 Hz and the duty cycle is 50%, the control unit 69 causes the light source unit 60 to emit light using the pulse width P1 in one field period (exposure A0) of the image sensor 212 by supplying a PWM control signal and a current value control signal, for which a light emission cycle of 600 Hz is set, to the light source driving unit 61. In this case, the first image processor 62 generates a pseudo image signal so as to establish the exposure amount of the latest pulse light emitted by the light source unit 60 in one field period of the image signal generated by the image sensor 212. That is, the brightness of the pseudo field based on the pseudo image signal generated by the first image processor 62 corresponds to the exposure amount of the latest pulse light when the light source unit 60 emits one pulse (for example, pulse light of pulse width P1, pulse light of pulse width P2, pulse light of pulse width P3, pulse light of pulse width P4) in each single field period.

In the case illustrated in FIG. 2, the brightness of the pseudo field may be represented by the following equation (1) when the duty cycle is a preset fixed value of 50%, for example.

$$\text{Brightness of pseudo field} = (1/(\text{light emission cycle})) \times \text{duty cycle} \quad (1)$$

For example, when a pulse width P1 and a light emission cycle of 600 Hz are set in one field period (exposure A0) of the image sensor 212, the brightness of the pseudo field (exposure A0) is as follows:

$$\text{The brightness of pseudo field } F1 = (1/600 \text{ Hz}) \times \text{duty cycle}.$$

Further, when a pulse width P2 and a light emission cycle of 300 Hz are set in the next one field period (exposure B0) of the image sensor 212, the brightness of the next pseudo field (exposure B0) is as follows:

$$\text{Brightness of pseudo field } F2 = (1/300 \text{ Hz}) \times \text{duty cycle}.$$

Thus, when the duty cycle is fixed, the light emission time is inversely proportional to the vocal cord vibrational frequency, and therefore a pseudo field-based image grows dark as the vocal cord vibrational frequency rises. Hence, when the vocal cord vibrational frequency is x, the control unit 69 multiplies the pseudo image signal by the gain of 0 dB in the following equation (2) and, by eliminating dependence on the vocal cord vibrational frequency, keeps the image brightness constant.

$$0 \text{ dB gain} = x \text{ Hz/frame rate (Hz) of image sensor } 212 \quad (2)$$

For example, in a case where, in one field period (exposure A0) of the image sensor 212, the gain amount, by which the pseudo field F1 or pseudo frame based on the pseudo image signal generated by the image sensor 212 is multiplied, is 0 dB and where the light emission cycle of vocal cord vibrations is 600 Hz and the frame rate of the image sensor 212 is 60 Hz, the equation is as follows.

$$0 \text{ db} = 600 \text{ Hz}/60 \text{ Hz}$$

Furthermore, the brightness of the output image based on the gain-adjusted pseudo image signal may be represented by the following equation (3):

$$\text{Output image brightness} = \text{pseudo field brightness} \times 0 \text{ dB gain} \quad (3)$$

That is, according to equations (1) and (2), the output image brightness = (1/60 Hz) × duty cycle.

Thus, as illustrated in FIG. 2, the control unit 69 sets, with respect to the AGC unit 64, a gain amount that corresponds to each pseudo field for the AGC unit 64 and causes the AGC unit 64 to multiply the pseudo image signal corresponding to each pseudo field by 0 dB (the gain amount). Accordingly, the image brightness may be kept constant by eliminating dependence on the vocal cord vibrational frequency.

Endoscope System Processing

Figure 3:
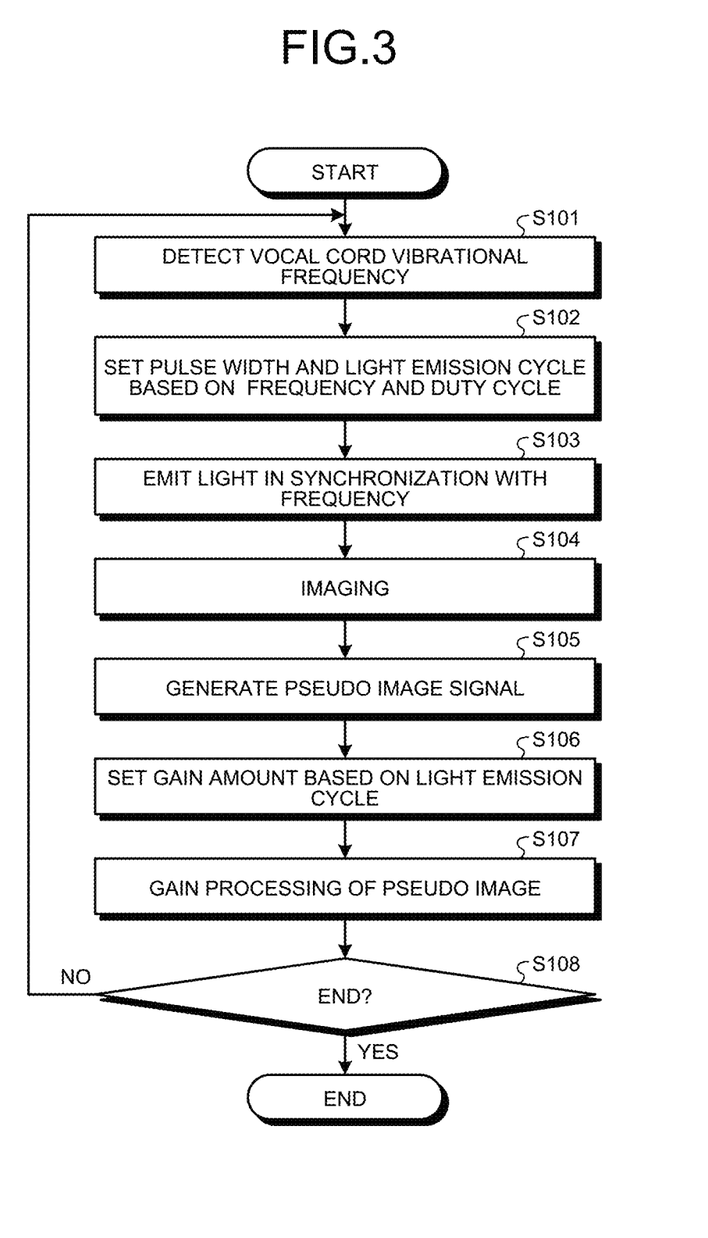
FIG. 3 is a flowchart illustrating an overview of processing executed by an endoscope system according to the first embodiment.

The processing executed by the endoscope system 1 will be described next. FIG. 3 is a flowchart illustrating an overview of processing executed by the endoscope system 1.

As illustrated in FIG. 3, the vocal cord frequency detection unit 67 first detects the vocal cord vibrational frequency based on a voice signal that is input from the voice input device 4 via the preprocessor 66 (step S101).

Next, the control unit 69 sets the pulse width and light emission cycle for when the light source unit 60 emits pulse light based on the vocal cord vibrational frequency detected by the vocal cord frequency detection unit 67 (step S102).

Thereafter, the control unit 69 causes the light source unit 60 to emit light in synchronization with the vocal cord vibrational frequency and using the pulse width and the light emission cycle which have been set in step S102 (step S103). Specifically, the control unit 69 causes the light source unit 60 to emit light in synchronization with the vocal cord vibrational frequency and using the pulse width and the light emission cycle set in step S102, by supplying a PWM control signal and a current value control signal, for which the pulse width and the light emission cycle have been set, to the light source driving unit 61.

Next, the control unit 69 causes the image sensor 212 to form an image as a result of receiving the reflected light from an object resulting from the light source unit 60 emitting pulse light (step S104). In this case, the image sensor 212 outputs an image signal to the first image processor 62.

Thereafter, the first image processor 62 generates a pseudo image signal by using an image signal that is input from the image sensor 212 and an image signal that is input from the image sensor 212 before the former image signal (step S105).

Next, the control unit 69 sets a gain amount using the AGC unit 64 based on the light emission cycle set in step S102 (step S106).

Thereafter, the AGC unit 64 amplifies the pseudo image signal which has been input from the first image processor 62 via the brightness detection unit 63, by the gain amount set by the control unit 69 and outputs the amplified signal to the second image processor 65 (step S107).

Subsequently, when an end signal to end the subject inspection has been input from the input device 3 (step S108: Yes), the endoscope system 1 ends the processing. In contrast, when an end instruction to end the subject inspection has not been input from the input device 3 (step S108: No), the endoscope system 1 returns to step S101 above.

According to the first embodiment, the control unit 69 sets, with respect to the AGC unit 64, a gain amount that corresponds to each pseudo field for the AGC unit 64 and causes the AGC unit 64 to multiply the pseudo image signal corresponding to each pseudo field by 0 dB (the gain amount), and therefore the image brightness may be kept constant irrespective of the vocal cord frequency.

Second Embodiment

A second embodiment will be described next. In addition to having a different configuration from the endoscope system 1 according to the first embodiment, an endoscope system according to the second embodiment utilizes a different method of generating a pseudo image signal as generated by the first image processing unit, and different brightness correction. After describing the configuration of the endoscope system according to the second embodiment hereinbelow, the method of generating a pseudo image signal as generated by the first image processing unit, and brightness correction, in the endoscope system according to the second embodiment will be described. Note that the same reference signs are assigned to the same configurations as in the endoscope system 1 according to the foregoing first embodiment and that detailed descriptions of these configurations are omitted.

Endoscope System Function Configuration

Figure 4:
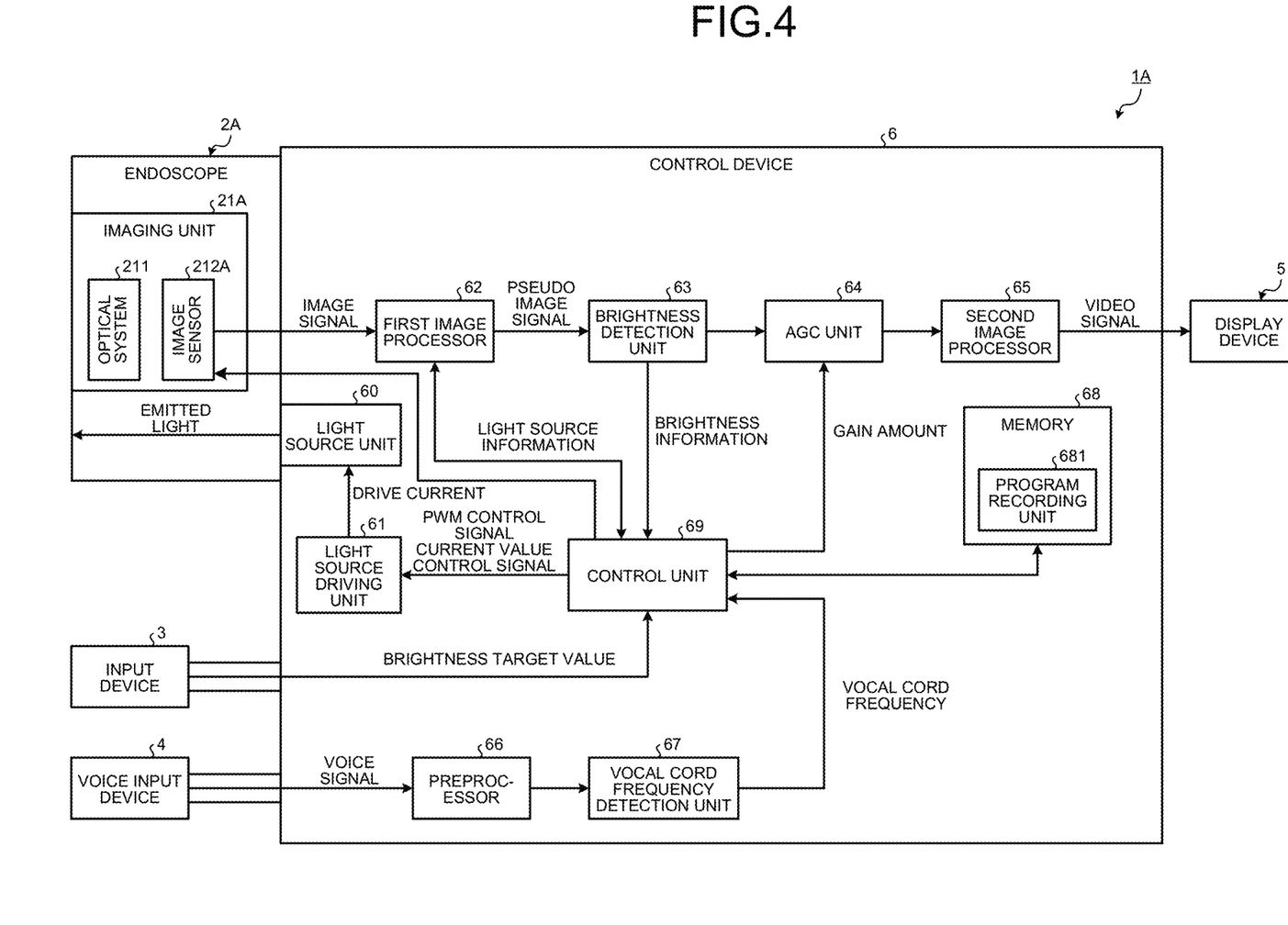
FIG. 4 is a block diagram illustrating a function configuration of an endoscope system according to a second embodiment.

FIG. 4 is a block diagram illustrating a function configuration of an endoscope system according to the second embodiment. The endoscope system 1A illustrated in FIG. 4 includes an endoscope 2A instead of the endoscope 2 of the endoscope system 1 according to the first embodiment hereinabove. The endoscope 2A includes an image sensor 212A instead of the image sensor 212 of the endoscope 2 according to the first embodiment hereinabove.

Based on control by the control device 6, the image sensor 212A receives the object image formed by the optical system 211 according to a predetermined frame rate and generates an image signal by photoelectrically converting the received object image. The image sensor 212A outputs the image signal to the control device 6. The image sensor 212A includes a progressive CMOS (Complementary Metal Oxide Semiconductor) sensor, or the like. The image sensor 212A has a plurality of pixels arranged in a two-dimensional matrix shape.

Method of Generating Pseudo Frames Using First Image Processing Unit

Figure 5:
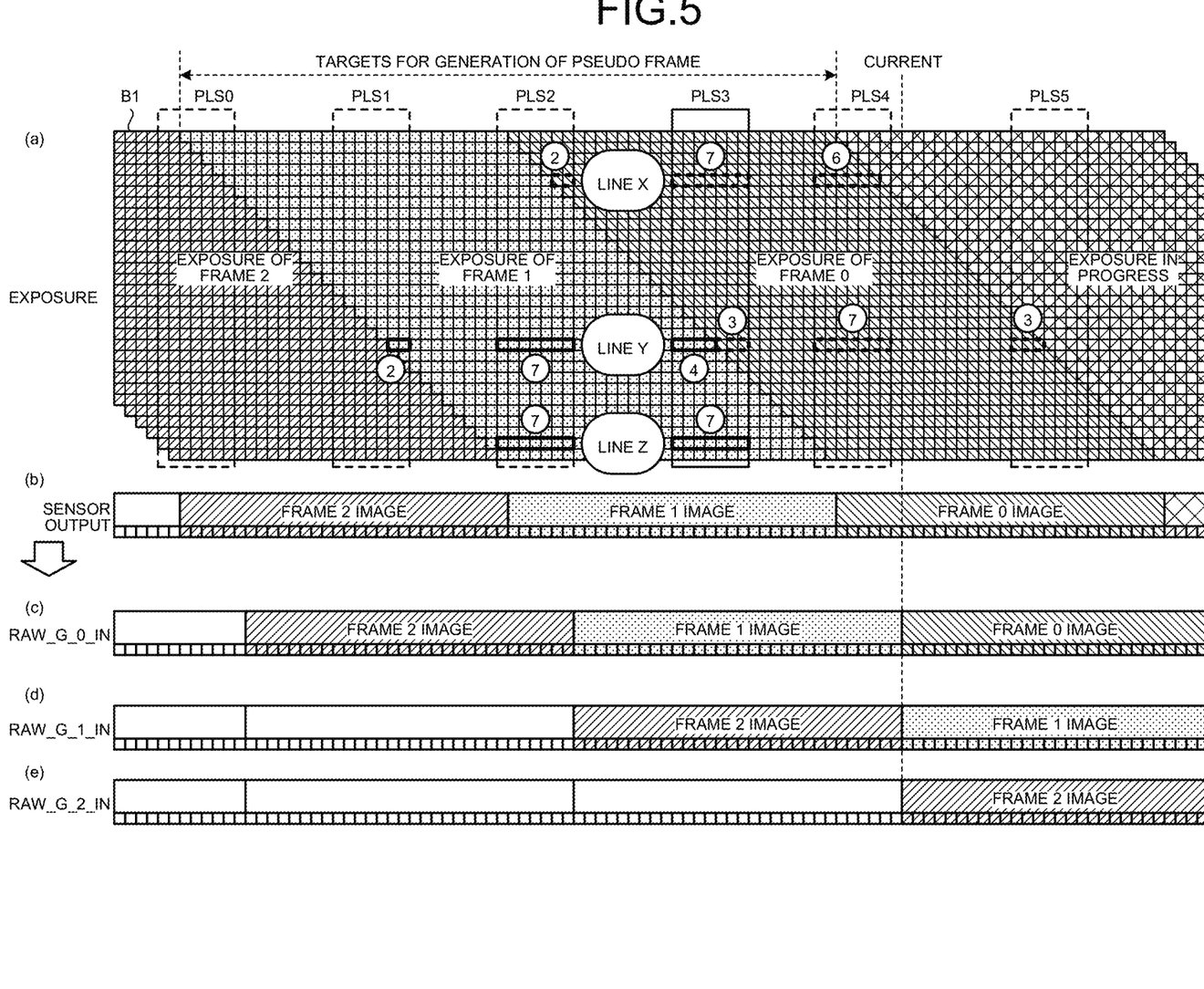
FIG. 5 is a diagram that schematically illustrates a method of generating a pseudo frame as performed by a first image processor according to the second embodiment.

A method of generating pseudo frames using the first image processor 62 for the image signal generated by the image sensor 212A will be described next. FIG. 5 is a diagram that schematically illustrates a method of generating pseudo frames using the first image processor 62. In FIG. 5, starting at the top, (a) illustrates exposure timing for each frame, (b) illustrates sensor outputs from the image sensor 212A, and (c) to (e) illustrate pseudo image signals of each line. Furthermore, in FIG. 5, pulse-like regions represent pulse light PLS0 to pulse light PLS5 as emitted by the light source unit 60. Furthermore, in FIG. 5, one rectangular block B1 corresponds to one line period in the vertical direction.

Case where Dimming is not Performed

First, a case where dimming of the pulse light emitted by the light source unit 60 is not performed will be described. The first image processor 62 selects generation-target pulse light from a cycle of at least two frames (a pseudo frame generation period), which has been input from the image sensor 212A) and provides the pseudo frame generation period in a cycle of at least two frames. Furthermore, the target pulse light is assumed to be the latest on the time axis and to be contained within the pseudo frame generation period. Specifically, as illustrated in FIG. 5, because only a portion of the pulse light PLS4 is contained in the pseudo frame generation period, the pulse light PLS3 is selected as the target pulse light. Hence, the first image processor 62 combines at least two frames' worth of the image signal at a ratio corresponding to the amount of exposure to pulse light, thereby generating pseudo frames based on the pseudo image signal.

Line X Case

First, a case involving line X illustrated in FIG. 5 will be described.

As illustrated in FIG. 5, line X is exposed in a two-line period by pulse light PLS2, in a seven-line period by pulse light PLS3, and in a six-line period by pulse light PLS4. Hence, the first image processor 62 calculates a [pseudo frame line X image] constituting a line-X pseudo frame by using equation (4) below, said image being regarded as an image that corresponds to exposure in a seven-line period by pulse light PLS3 in a [RAW_G_0_IN line X image].

$$[\text{PSEUDO FRAME LINE } X \text{ IMAGE}] = \frac{7}{2+7+6}[\text{RAW\_G\_0\_IN LINE } X \text{ IMAGE}] \quad (4)$$

Line Y Case

Next, a case involving a line Y as illustrated in FIG. will be described.

As illustrated in FIG. 5, line Y is exposed in a two-line period by pulse light PLS1, in a seven-line period by pulse light PLS2, and in a four-line period by pulse light PLS3. In addition, line Y is exposed in a three-line period by pulse light PLS3, in a seven-line period by pulse light PLS4, and in a three-line period by pulse light PLS5. Hence, the first image processor 62 calculates a [pseudo frame line Y image] constituting a line-Y pseudo frame by using equation (5) below, said image being regarded as an image obtained by combining an image that corresponds to exposure in a four-line period by pulse light PLS3 in a [RAW_G_1_IN line X image] with an image that corresponds to exposure in a three-line period by pulse light PLS3 in a [RAW_G_0_IN line X image].

$$[\text{PSEUDO FRAME LINE } Y \text{ IMAGE}] = \quad (5)$$
$$\frac{4}{2+7+4}[\text{RAW\_G\_1\_IN LINE } X \text{ IMAGE}] + \frac{3}{3+7+3}[\text{RAW\_G\_0\_IN LINE } X \text{ IMAGE}]$$

Line Z Case

Next, a case involving a line Z as illustrated in FIG. will be described.

As illustrated in FIG. 5, line Z is exposed in a seven-line period by pulse light PLS2, and in a seven-line period by pulse light PLS3. Hence, the first image processor 62 calculates a [pseudo frame line Z image] constituting a line-Z pseudo frame by using equation (6) below, said image being regarded as an image that corresponds to exposure in a seven-line period by pulse light PLS3 in a [frame one-line Z image].

$$[\text{PSEUDO FRAME LINE } Z \text{ IMAGE}] = \frac{7}{7+7}[\text{RAW\_G\_1\_IN LINE } X \text{ IMAGE}] \quad (6)$$

Case where Dimming is Performed

Next, a case where dimming of the pulse light emitted by the light source unit 60 is performed will be described. The first image processor 62 generates a pseudo frame through summation according to the ratio between the exposure amounts of the respective pulse light. Specifically, when there is no dimming of the light source unit 60, the first image processor 62 generates a pseudo frame by using exposure amounts as light emission periods, but when dimming of the light source unit 60 is performed, the first image processor 62 generates a pseudo frame by multiplying light amounts in light emission periods by the exposure amounts. Hence, the first image processor 62 calculates a [pseudo frame line X image], a [pseudo frame line Y image], and a [pseudo frame line Z image] by using equations (7) to (9) below.

$$[\text{PSEUDO FRAME LINE } X \text{ IMAGE}] = \quad (7)$$
$$\frac{7*PLS3 \text{ LIGHT AMOUNT}}{2*PLS2 \text{ LIGHT AMOUNT} + 7*PLS3 \text{ LIGHT AMOUNT} + 6*PLS4 \text{ LIGHT AMOUNT}}[\text{RAW\_G\_0\_IN LINE } X \text{ IMAGE}]$$

$$[\text{PSEUDO FRAME LINE } Y \text{ IMAGE}] = \quad (8)$$
$$\frac{4*PLS3 \text{ LIGHT AMOUNT}}{2*PLS1 \text{ LIGHT AMOUNT} + 7*7*PLS2 \text{ LIGHT AMOUNT} + 4*PLS3 \text{ LIGHT AMOUNT}}[\text{RAW\_G\_1\_IN LINE } X \text{ IMAGE}] +$$
$$\frac{3*PLS3 \text{ LIGHT AMOUNT}}{3*PLS3 \text{ LIGHT AMOUNT} + 7*PLS4 \text{ LIGHT AMOUNT} + 3*PLS5 \text{ LIGHT AMOUNT}}[\text{RAW\_G\_0\_IN LINE } X \text{ IMAGE}]$$

$$[\text{PSEUDO FRAME LINE } Z \text{ IMAGE}] = \quad (9)$$
$$\frac{7*PLS3 \text{ LIGHT AMOUNT}}{7*PLS2 \text{ LIGHT AMOUN} + 7*PLS3 \text{ LIGHT AMOUNT}}[\text{RAW\_G\_1\_IN LINE } X \text{ IMAGE}]$$

Thus, the first image processor 62 uses an image signal of at least two frames to generate a pseudo frame (a pseudo image) based on a pseudo image signal that corresponds to the pulse light of one pulse.

Overview of Brightness Correction

Figure 6:
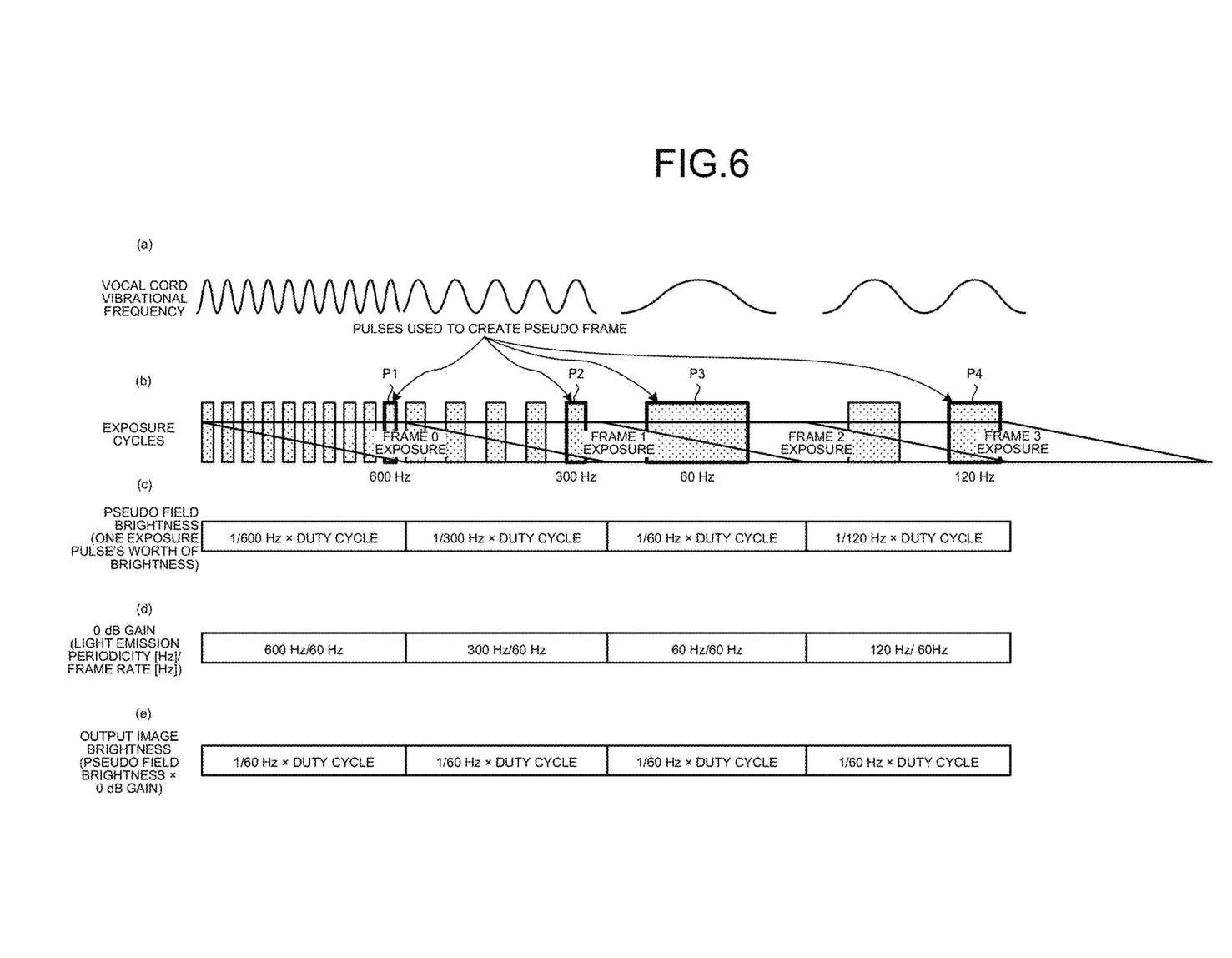
FIG. 6 is a diagram illustrating an overview of a correction method of correcting the brightness of a pseudo frame based on a pseudo image signal as performed by a control unit according to the second embodiment.

A method of correcting the brightness of a pseudo frame based on a pseudo image signal as performed by the control unit 69 will be described next. FIG. 6 is a diagram illustrating an overview of a correction method of correcting the brightness of a pseudo frame based on a pseudo image signal as performed by the control unit 69. In FIG. 6, starting at the top, (a) illustrates the vocal cord vibrational frequency, (b) illustrates the exposure period (light emission cycle (light emission frequency) and pulse width (light emission time) in one frame of the image sensor 212), (c) illustrates the brightness of one frame based on a pseudo image signal, (d) illustrates 0 dB (gain amount) (light emission periodicity [Hz]/frame rate [Hz]) by the AGC unit 64, and (e) illustrates the output image brightness (pseudo frame brightness×0 dB gain).

As illustrated in FIG. 6, as per the foregoing first embodiment, the control unit 69 sets a pulse width and a light emission cycle for when the light source unit 60 emits pulse light in the frame period (exposure 0) of the image sensor 212A, based on the vocal cord vibrational frequency detected by the vocal cord frequency detection unit 67 and the duty cycle, and causes the light source unit 60 to emit light using the set pulse width and light emission cycle. The control unit 69 sets, for the AGC unit 64, a gain amount that corresponds to each pseudo frame for the AGC unit 64 and causes the AGC unit 64 to multiply the pseudo image signal corresponding to each pseudo frame by 0 dB (the gain amount). Accordingly, the image brightness may be kept constant by eliminating dependence on the vocal cord vibrational frequency.

According to the second embodiment, the control unit 69 sets, for the AGC unit 64, a gain amount that corresponds to each pseudo field for the AGC unit 64 and causes the AGC unit 64 to multiply the pseudo image signal corresponding to each pseudo field by 0 dB (the gain amount), and therefore the image brightness may be kept constant irrespective of the vocal cord frequency.

Furthermore, according to the second embodiment, the first image processor 62 uses an image signal of at least two frames to generate a pseudo frame (a pseudo image) based on a pseudo image signal that corresponds to the pulse light of one pulse, and therefore the image brightness suitable for observation may be kept constant.

In addition, according to the second embodiment, when the first image processor 62 generates the pseudo frame, it is possible to reliably prevent exposure unevenness because a specified pulse-light light emission period is, in one field period or one frame period of the image sensor 212A, the period of the latest pulse light emitted by the light source unit 60 and is the period in which the pseudo image signal is generated.

Further Embodiments

By suitably combining a plurality of constituent elements which are disclosed in the endoscope systems according to the foregoing first and second embodiments of the present disclosure, various embodiments may be configured. For example, several constituent elements may be removed from among all the constituent elements disclosed in the endoscope systems according to the foregoing first and second embodiments of the present disclosure. Moreover, the constituent elements described in the endoscope systems according to the foregoing first and second embodiments of the present disclosure may also be suitably combined.

Furthermore, "parts" mentioned earlier in the endoscope systems according to the first and second embodiments of the present disclosure may also be replaced with the wording "means" and "circuits", and so forth. For example, "control unit" may be replaced with "control means" or "control circuit".

In addition, a program that is executed by the endoscope systems according to the first and second embodiments of the present disclosure is file data that is in an installable format or an executable format and that is provided by being recorded on a recording medium that is computer-readable, such as a CD-ROM, a flexible disk (FD), a CD-R, a digital versatile disk (DVD), a USB medium, or a flash memory.

Furthermore, a program that is executed by the endoscope systems according to the first and second embodiments of the present disclosure may be configured to be stored on a computer connected to a network such as the internet or to be provided by being downloaded over the internet.

Note that, although expressions such as "first", "thereafter", and "next" are used in the flowchart descriptions in the present specification to illustrate the pre- and post-processing relationships between steps, the sequence of the processing for carrying out the present disclosure is not necessarily uniquely defined by such expressions. In other words, the sequence of the processing in the flowcharts disclosed in the present specification may be revised within a consistent scope.

The present disclosure exhibits an advantageous effect of enabling image brightness to be maintained constant regardless of a vocal cord frequency.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A control device comprising:
a memory; and
processing circuitry configured to:
control an image sensor including a plurality of pixels arranged in a two-dimensional matrix to generate an image signal by performing imaging sequentially according to predetermined frames;
detect a frequency of vocal cord vibration of a subject based on a voice signal input from an external device;
set, for a light source configured to intermittently emit pulse light according to a pulse current, a pulse width and a light emission cycle for when the light source emits light, based on the frequency of the vocal cord vibration and a preset duty cycle;
control the light source to emit the pulse light using the pulse width and the light emission cycle in one field period or one frame period of the image sensor in synchronization with the frequency of the vocal cord vibration;
calculate, based on the light emission cycle or the frequency of the vocal cord vibration, a gain amount by which the image signal is to be multiplied;
generate a pseudo image signal that corresponds to the image signal when the plurality of pixels are exposed in a specified pulse-light light emission period, based on the image signal generated by the image sensor; and
multiply the pseudo image signal by the gain amount, wherein
the specified pulse-light light emission period is, in one field period or one frame period of the image sensor, the period of the latest pulse light emitted by the light source and the period in which the pseudo image signal is generated.

2. The control device according to claim 1, wherein the processing circuitry is configured to:
generate the pseudo image signal based on two or more temporally consecutive image signals generated by the image sensor.

3. The control device according to claim 1, wherein the image sensor is a CCD sensor.

4. The control device according to claim 1, wherein the image sensor is a CMOS sensor.

5. A medical observation system comprising:
the control device according to claim 1;
an endoscope including the image sensor configured to generate the image signal, the image sensor being disposed at an end portion of an insertable section inserted into a subject; and
a voice input device configured to receive a voice input and generate the voice signal, wherein, by supplying pulse light to the endoscope, the light source is configured to project the pulse light toward the object from the end.

6. A control method, comprising:
controlling an image sensor having a plurality of pixels arranged in a two-dimensional matrix shape to generate an image signal by performing imaging sequentially according to predetermined frames;
detecting a frequency of vocal cord vibration of a subject based on a voice signal which is input from an external device;
setting, for a light source configured to intermittently emit pulse light according to a pulse current, a pulse width and a light emission cycle for when the light source emits light, based on the frequency of the vocal cord vibration and a preset duty cycle;
controlling the light source to emit the pulse light using the pulse width and the light emission cycle in one field period or one frame period of the image sensor in synchronization with the frequency of the vocal cord vibration;
calculating, based on the light emission cycle or the frequency of the vocal cord vibration, a gain amount by which the image signal is to be multiplied;
generating a pseudo image signal that corresponds to the image signal when the plurality of pixels are exposed in a specified pulse-light light emission period, based on the image signal generated by the image sensor; and
multiplying the pseudo image signal by the gain amount, wherein
the specified pulse-light light emission period is, in one field period or one frame period of the image sensor, the period of the latest pulse light emitted by the light source and the period in which the pseudo image signal is generated.

7. A non-transitory computer-readable recording medium including executable instructions, which when executed by a computer cause the computer to execute a control method, the control method comprising:
controlling an image sensor having a plurality of pixels arranged in a two-dimensional matrix shape to generate an image signal by performing imaging sequentially according to predetermined frames;
detecting a frequency of vocal cord vibration of a subject based on a voice signal which is input from an external device;
setting, for a light source configured to intermittently emit pulse light according to a pulse current, a pulse width and a light emission cycle for when the light source emits light, based on the frequency of the vocal cord vibration and a preset duty cycle;
controlling the light source to emit the pulse light using the pulse width and the light emission cycle in one field period or one frame period of the image sensor in synchronization with the frequency of the vocal cord vibration;
calculating, based on the light emission cycle or the frequency of the vocal cord vibration, a gain amount by which the image signal is to be multiplied;
generating a pseudo image signal that corresponds to the image signal when the plurality of pixels are exposed in a specified pulse-light light emission period, based on the image signal generated by the image sensor; and
multiplying the pseudo image signal by the gain amount, wherein
the specified pulse-light light emission period is, in one field period or one frame period of the image sensor, the period of the latest pulse light emitted by the light source and the period in which the pseudo image signal is generated.

8. The control method according to claim 6, wherein the pseudo image signal is generated based on two or more temporally consecutive image signals generated by the image sensor.

9. The non-transitory computer-readable recording medium according to claim 7, wherein the pseudo image signal is generated based on two or more temporally consecutive image signals generated by the image sensor.

* * * * *